(12) United States Patent
Whipple et al.

(10) Patent No.: US 10,123,825 B2
(45) Date of Patent: Nov. 13, 2018

(54) SACROILIAC SCREW

(71) Applicant: Amendia, Inc., Marietta, GA (US)

(72) Inventors: Dale Whipple, Woodstock, GA (US); Jason Hayes Tillett, Atlanta, GA (US); John G. Keating, Atlanta, GA (US); Jon Potter Kimball, Chapel Hill, NC (US); Ralph Arthur Liebelt, Durham, NC (US)

(73) Assignee: Amendia, Inc., Marietta, GA (US)

( * ) Notice: Subject to any disclaimer, the term of this patent is extended or adjusted under 35 U.S.C. 154(b) by 0 days.

(21) Appl. No.: 15/918,459

(22) Filed: Mar. 12, 2018

(65) Prior Publication Data

US 2018/0235669 A1    Aug. 23, 2018

Related U.S. Application Data

(60) Division of application No. 14/856,879, filed on Sep. 17, 2015, now Pat. No. 9,943,340, which is a continuation-in-part of application No. 14/630,748, filed on Feb. 25, 2015, now Pat. No. 9,358,057.

(51) Int. Cl.
  *A61B 17/70*  (2006.01)
  *A61B 17/86*  (2006.01)
  *A61B 17/56*  (2006.01)

(52) U.S. Cl.
  CPC ........ *A61B 17/7055* (2013.01); *A61B 17/861* (2013.01); *A61B 17/864* (2013.01); *A61B 17/8605* (2013.01); *A61B 17/8615* (2013.01); *A61B 17/8635* (2013.01); *A61B 17/8685* (2013.01); *A61B 17/8695* (2013.01); *A61B 2017/564* (2013.01); *A61B 2017/8655* (2013.01)

(58) Field of Classification Search
  CPC ..... A61B 17/70; A61B 17/7055; A61B 17/16; A61B 17/1637; A61B 17/86; A61B 17/864; A61B 17/861
  See application file for complete search history.

(56) References Cited

U.S. PATENT DOCUMENTS

| | | | |
|---|---|---|---|
| 6,019,760 A | 2/2000 | Metz-Stavenhagen et al. | |
| 6,053,916 A | 4/2000 | Moore | |
| 6,402,757 B1 | 6/2002 | Moore | |
| 6,635,059 B2 * | 10/2003 | Randall | A61B 17/683 606/304 |
| 8,529,609 B2 | 9/2013 | Helgerson et al. | |

(Continued)

FOREIGN PATENT DOCUMENTS

CN    102793579    11/2012

*Primary Examiner* — Christopher Beccia
(74) *Attorney, Agent, or Firm* — David L. King

(57) ABSTRACT

An improved joint fusion screw for transiliac fixation has a screw head and extending therefrom an elongate hollow shaft. The hollow shaft has an externally threaded end portion extending to a tip end and a non-externally threaded shank portion having a plurality of window openings. At or near the tip end is a start of a thread with a bone cutting flute. The bone cutting flute has a cutting edge on a circumferential exterior of the threaded tip to cut bone and directs the cut bone internally into a bone receiving opening in the hollow shaft directly in front of the cutting flute. The cutting edge lies at the start of the thread extending radially above the bone receiving opening at least partially overhanging the opening configured to cut bone.

3 Claims, 17 Drawing Sheets

(56) References Cited

U.S. PATENT DOCUMENTS

| | | |
|---|---|---|
| 8,808,377 B2 | 8/2014 | Donner |
| 8,894,685 B2 | 11/2014 | Mickiewicz et al. |
| 2006/0155286 A1 | 7/2006 | Wang |
| 2007/0233123 A1 | 10/2007 | Ahmad et al. |
| 2009/0192551 A1 | 7/2009 | Cianfrani et al. |
| 2010/0211113 A1 | 8/2010 | Olson |
| 2011/0137352 A1* | 6/2011 | Biedermann ...... A61B 17/8635 606/305 |
| 2011/0190830 A1 | 8/2011 | Biedermann |
| 2012/0095515 A1 | 4/2012 | Hamilton |
| 2012/0197311 A1 | 8/2012 | Kirchman |
| 2012/0323285 A1 | 12/2012 | Assell et al. |
| 2013/0018427 A1 | 1/2013 | Pham et al. |
| 2014/0121707 A1 | 5/2014 | Stark |
| 2014/0257409 A1 | 9/2014 | Reed |
| 2014/0277188 A1 | 9/2014 | Poulos |

* cited by examiner

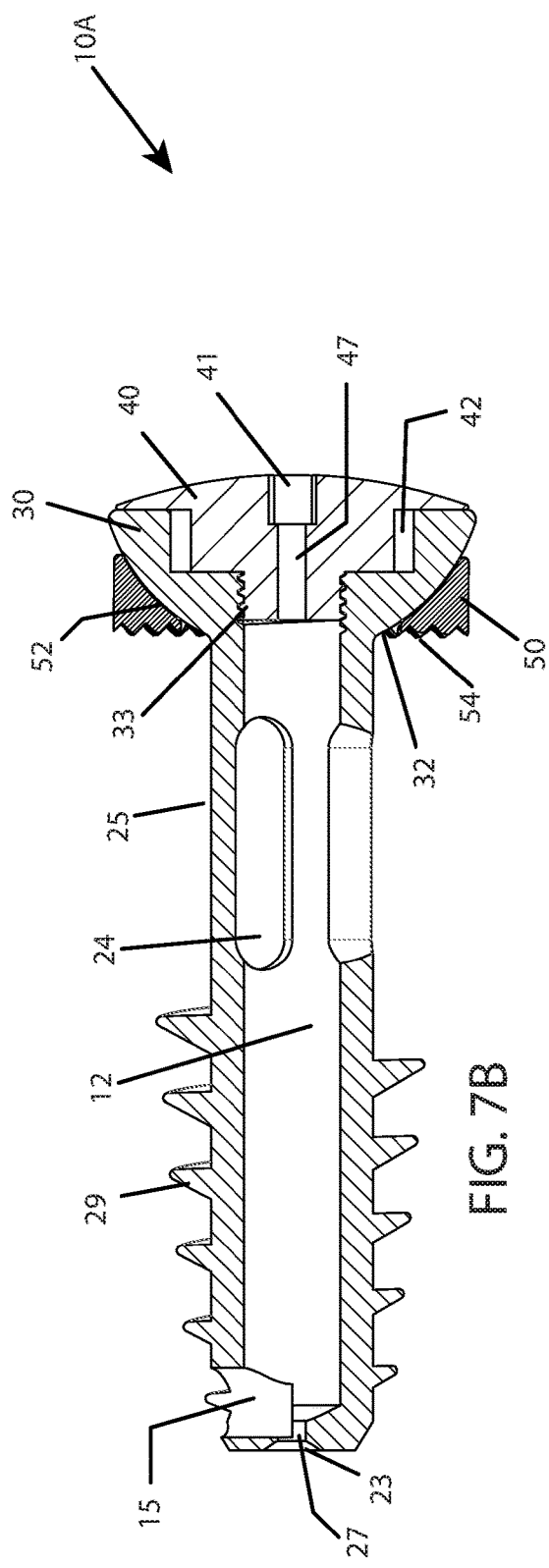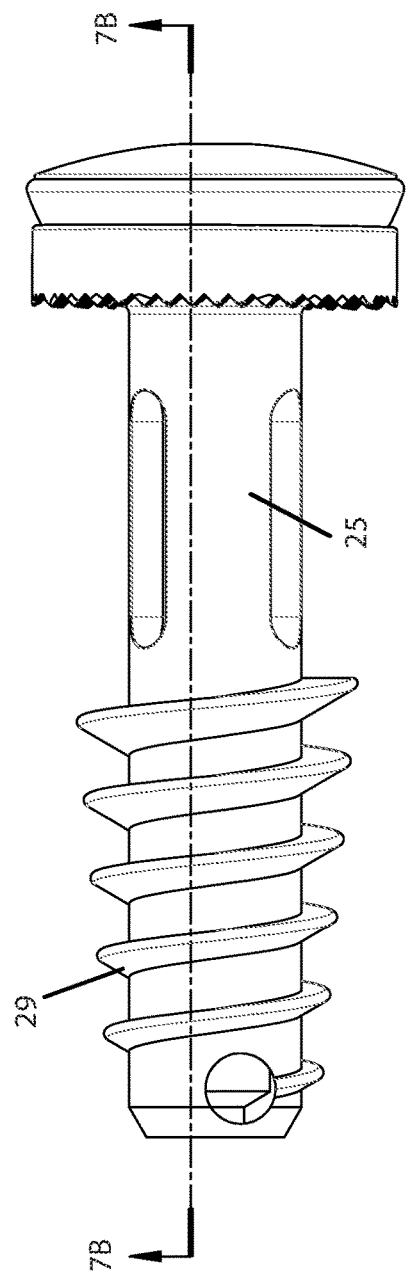
FIG. 7B
FIG. 7A

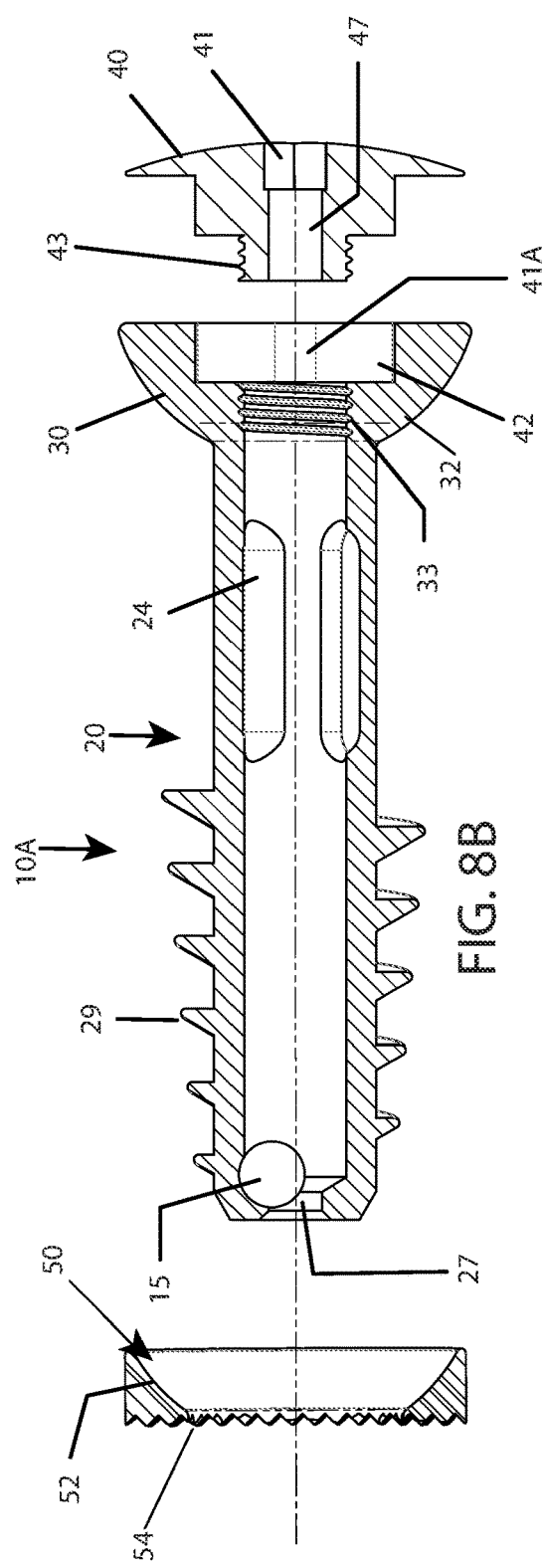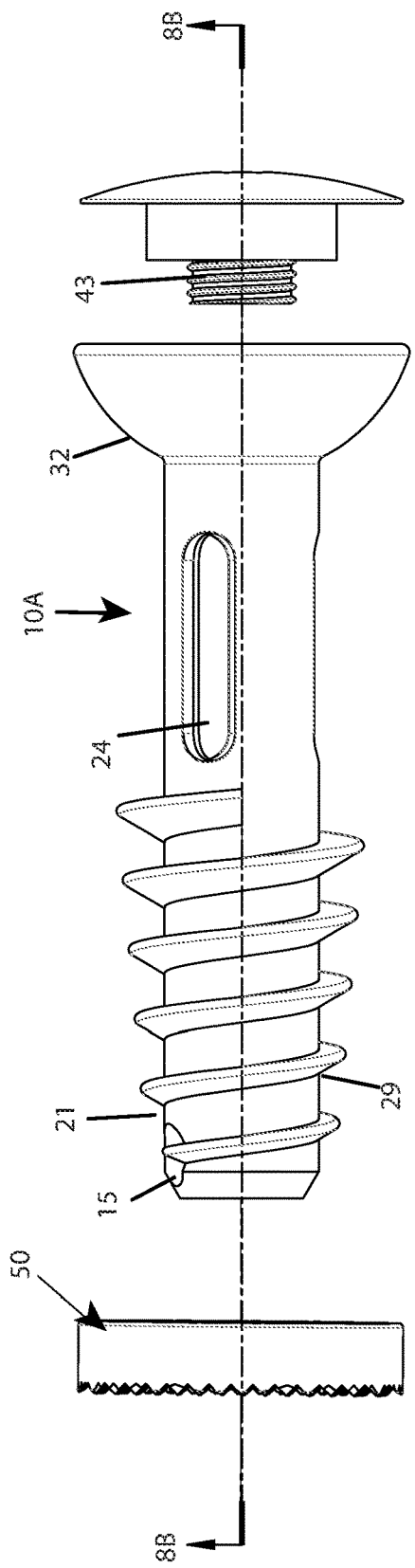
FIG. 8B
FIG. 8A

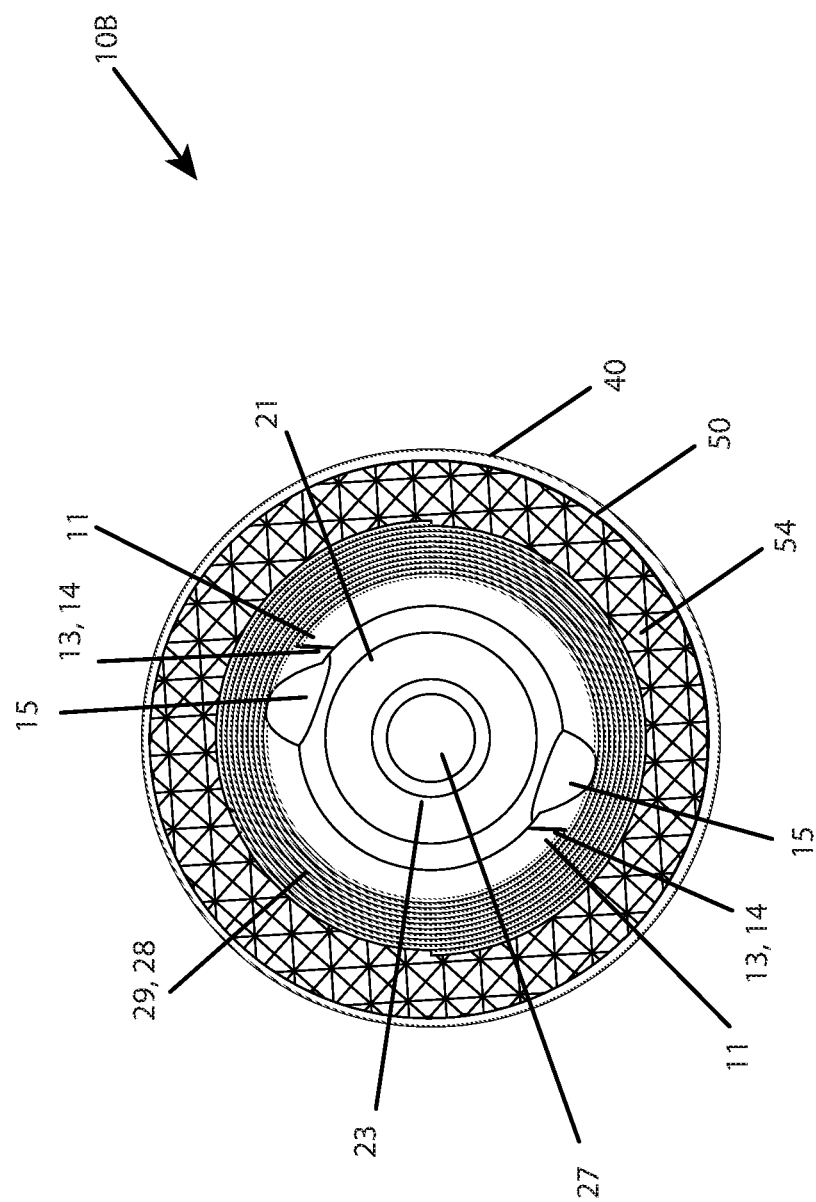

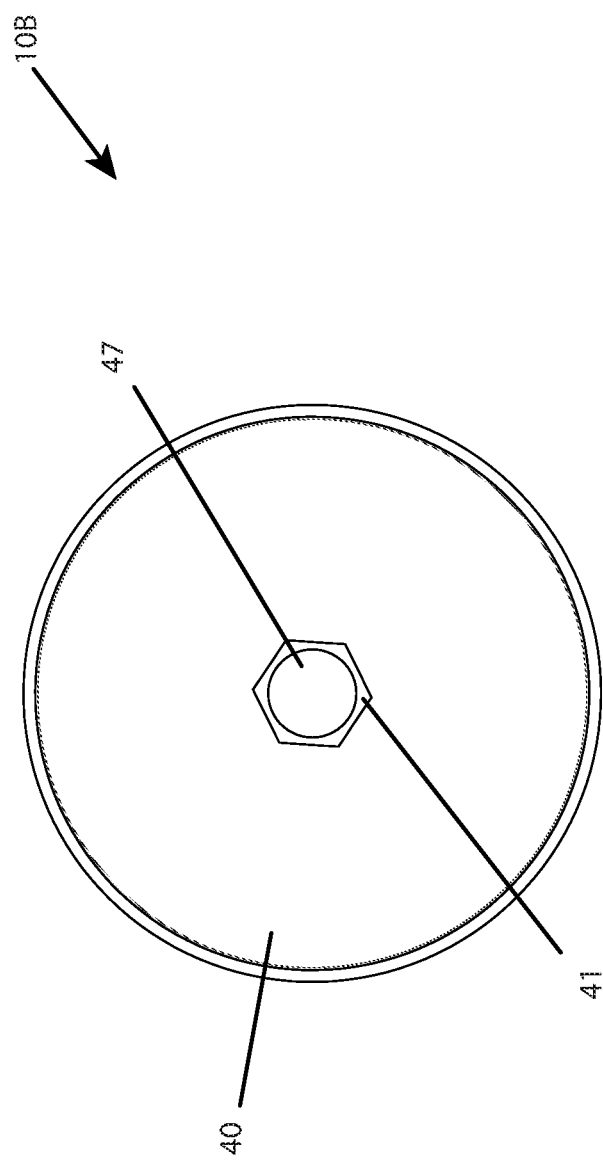

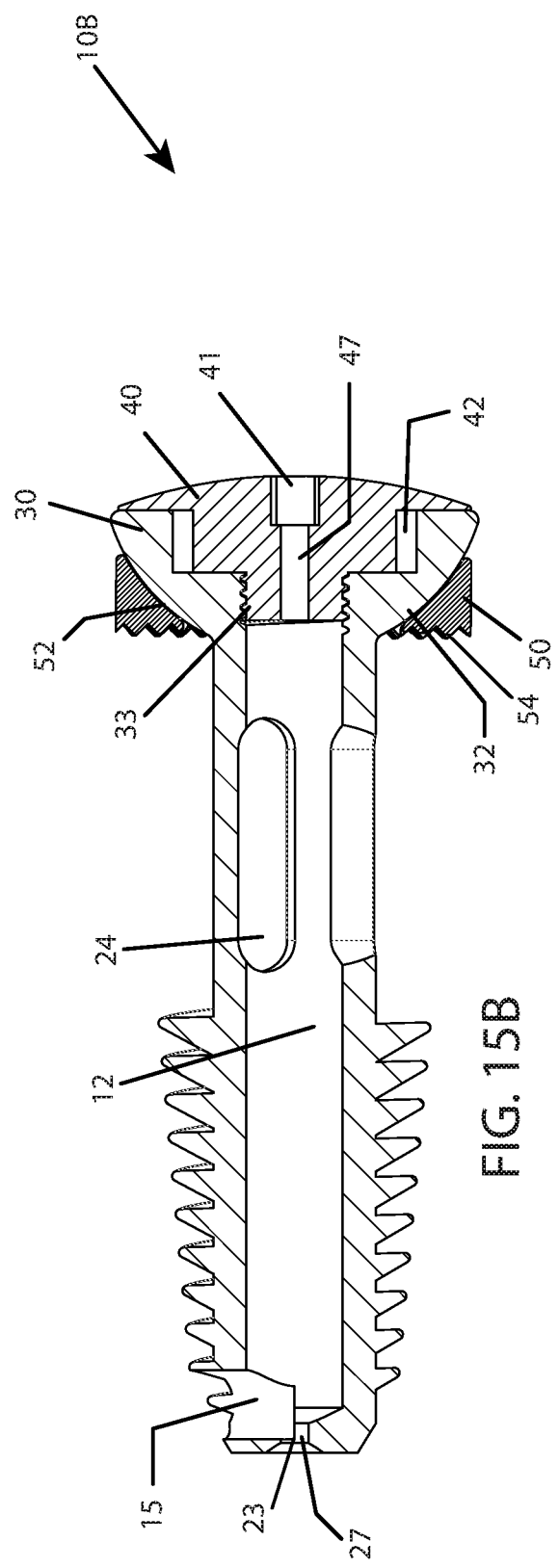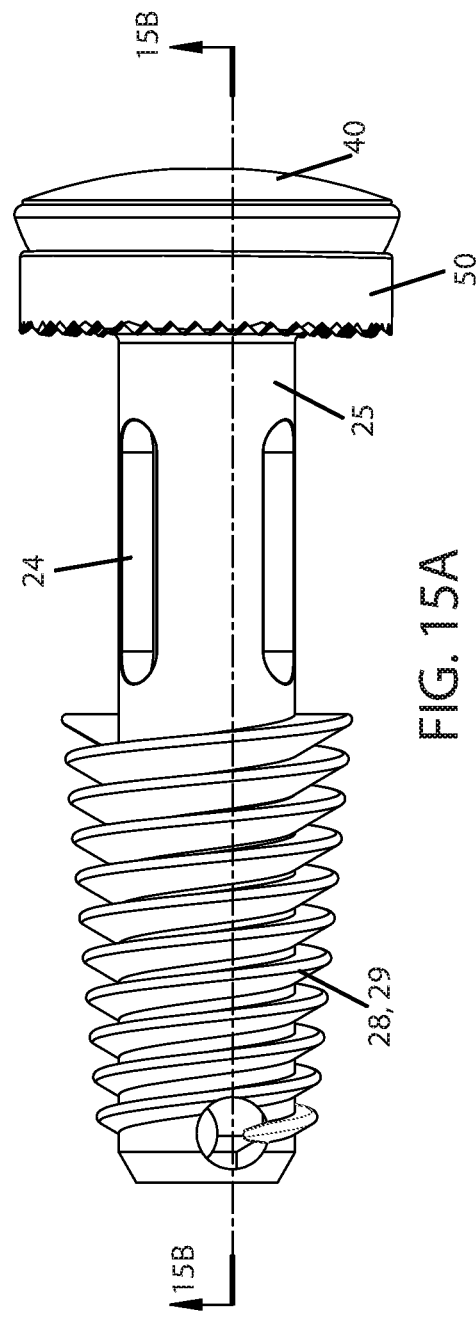

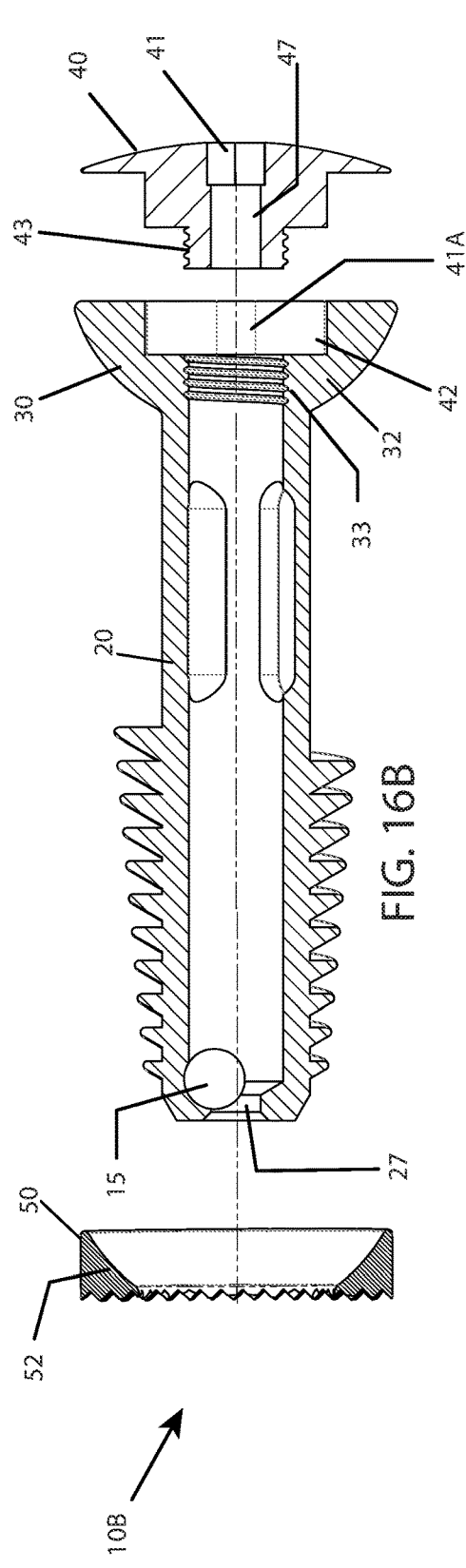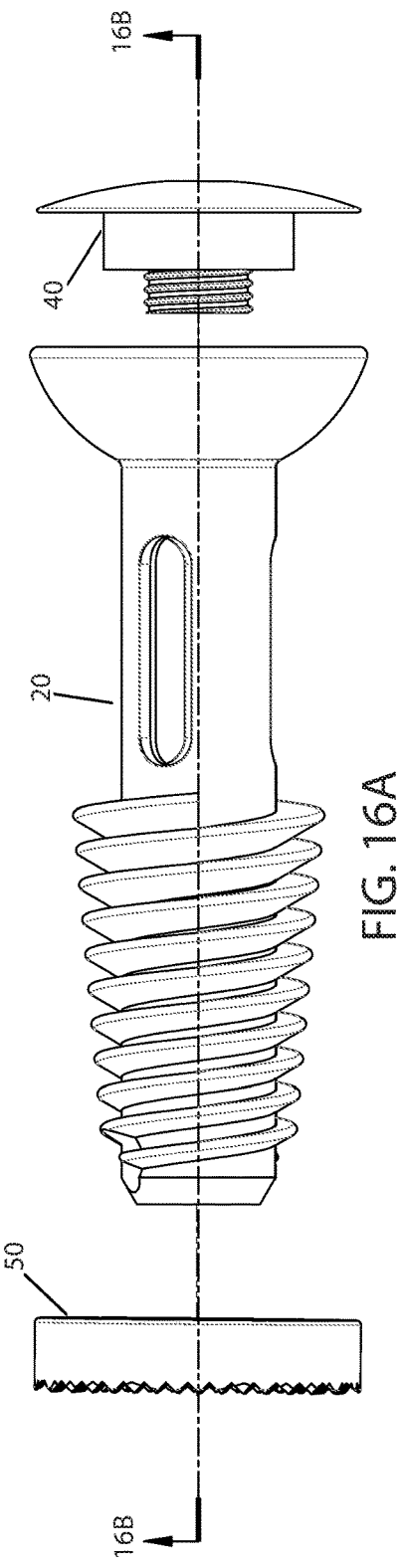

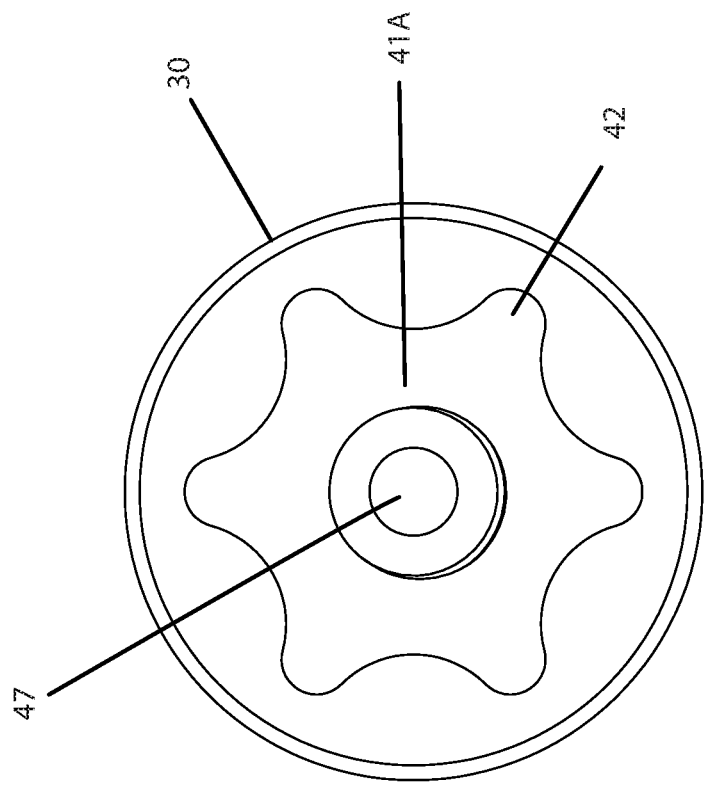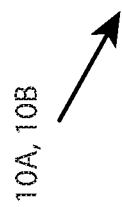
FIG. 17

SACROILIAC SCREW

RELATED APPLICATIONS

This application is a division of U.S. application Ser. No. 14/856,879 filed on Sep. 17, 2015 which is a continuation in part of U.S. application Ser. No. 14/630,748 entitled "Improved Sacroiliac Screw" filed Feb. 25, 2015.

TECHNICAL FIELD

The present invention relates to an improved spinal fixation screw for transiliac fixation and a method of use.

BACKGROUND OF THE INVENTION

Many complaints of lower back pain and leg pain have been attributed to herniated discs or other injuries to the spinal column. Extensive therapy and treatment has often been unsuccessful in alleviating such pain. It has been established that some of this lower back and leg pain can be attributed to symptomatic sacroiliac dysfunction or instability. Normally, the sacroiliac joint which spans between the sacrum bone and ilium bone has nutation of one to two degrees. "Nutation" is the medical term which describes the relative movement between the sacrum and ilium. A patient's sacroiliac joint can become damaged resulting in hypermobility of the joint. Because of the small range of motion in the sacroiliac joint, hypermobility is very difficult to diagnose. Therefore, lower back pain or leg pain caused by sacroiliac dysfunction often goes misdiagnosed or undiagnosed.

Accordingly, it is an objective of this invention to provide a device for correcting symptomatic sacroiliac dysfunction or instability. It is another aspect of this invention to provide a device which enhances stability and compression for purposes of immobilizing a joint, and for fusing two opposed bone structures across the joint.

SUMMARY OF THE INVENTION

An improved joint fusion screw for transiliac fixation has a screw head and extending therefrom an elongate hollow shaft. The hollow shaft has an externally threaded end portion extending to a tip end and a non-externally threaded shank portion having a plurality of window openings. At or near the tip end is a start of a thread with a bone cutting flute. The bone cutting flute has a cutting edge on a circumferential exterior of the threaded tip to cut bone and directs the cut bone internally into a bone receiving opening in the hollow shaft directly in front of the cutting flute. The cutting edge lies at the start of the thread extending radially above the bone receiving opening at least partially overhanging the opening configured to receive bone fragments.

In each embodiment, the hollow shaft has a bone chamber for receiving the cut bone fragments. The bone chamber extends to at least the window openings of the shank portion. Autograft cut bone fragments are directed to the window openings to enhance new bone growth and rapid fusion of the fusion screw. Preferably, the window openings of the shank portion are elongated slots.

The screw has an enlarged flat head with a convex rounded or hemispherical polyaxial bottom affixed or integral to an end of the shank. The end of the flat head has internal or female threads for receiving a threaded driver cap. The threaded driver cap has a cannulated opening or aperture for passing a guide wire and a torquing tool receiving cavity to thread the screw into the bone. The drive cap is affixed into the threaded end of the shank. The driver cap can be removably attached to allow bone packing material to be packed into the hollow shaft after screw insertion into the bone.

In one embodiment, the bone cutting flute has an ramp extending outwardly from the cutting edge forward of the thread at least partially overhanging the opening toward an inside diameter of the hollow shaft. The cut bone fragments are cut and re-directed internal along the ramps upon implantation of the screw into the bone receiving opening and into the hollow shaft. The cutting edge, instead of forming spiral cut autograft bone upon screw implantation, breaks the bone as it is redirected by the ramp. The spiral cut autograft bone fragments are pushed upwardly into the shaft toward the window openings.

In a second embodiment, at least two cutting flutes extend starting from the tip end longitudinally through two thread starts.

In a third embodiment, the tip end can have an annular ledge extending across the hollow shaft. The ledge has an aperture for receiving a guide wire. The aperture is coaxial with an axis of the screw and the aperture of the cap driver.

A method of transiliac fixation using the improved screw comprises the steps of pre-drilling an opening in the sacrum and the ilium bones to be fixed with a pilot hole opening and inserting a joint fixation screw with a hollow shaft onto the pre-drilled opening while cutting autograft bone fragments directed into the hollow shaft. The hollow shaft has a bone receiving chamber extending to a plurality of window openings further in the hollow shaft and the step of threading of the screw directs the autograft bone fragments to an opening to enhance fusion. The screw can have apertures at the tip end and at the driver cap and the method may further comprise the steps of inserting a guide wire to create a drill path, inserting a cannulated drill over the guide wire to pre-drill the pilot hole, and then inserting the screw onto the guide wire to direct the path for insertion into the bone.

BRIEF DESCRIPTION OF THE DRAWINGS

The invention will be described by way of example and with reference to the accompanying drawings in which:

FIG. 7A is a side view of the present invention.

FIG. 7B is a cross-sectional view taken along lines 7B-7B of FIG. 7A.

FIG. 8A is an exploded view of the first embodiment of the present invention showing the washer, the screw body and an end cap at the screw head portion.

FIG. 8B is a cross-sectional view taken along lines 8B-8B of FIG. 8A.

FIG. 10 is an end view showing the dual threaded shank of the present invention of the second embodiment of the present invention.

FIG. 11 is a top view of the second embodiment of the present invention.

FIG. 15A is a side view of the second embodiment of the present invention.

FIG. 15B is a cross-sectional view taken along lines 15B-15B of FIG. 15A.

FIG. 16A is a side view of the second embodiment of the present invention.

FIG. 16B is a cross-sectional view taken along lines 16B-16B of FIG. 16A.

FIG. 17 is a top view of the screw regardless of the embodiment where the end cap has been removed exposing the screw slot and cannulation for implanting the screw body.

DETAILED DESCRIPTION OF THE INVENTION

Figure 4:
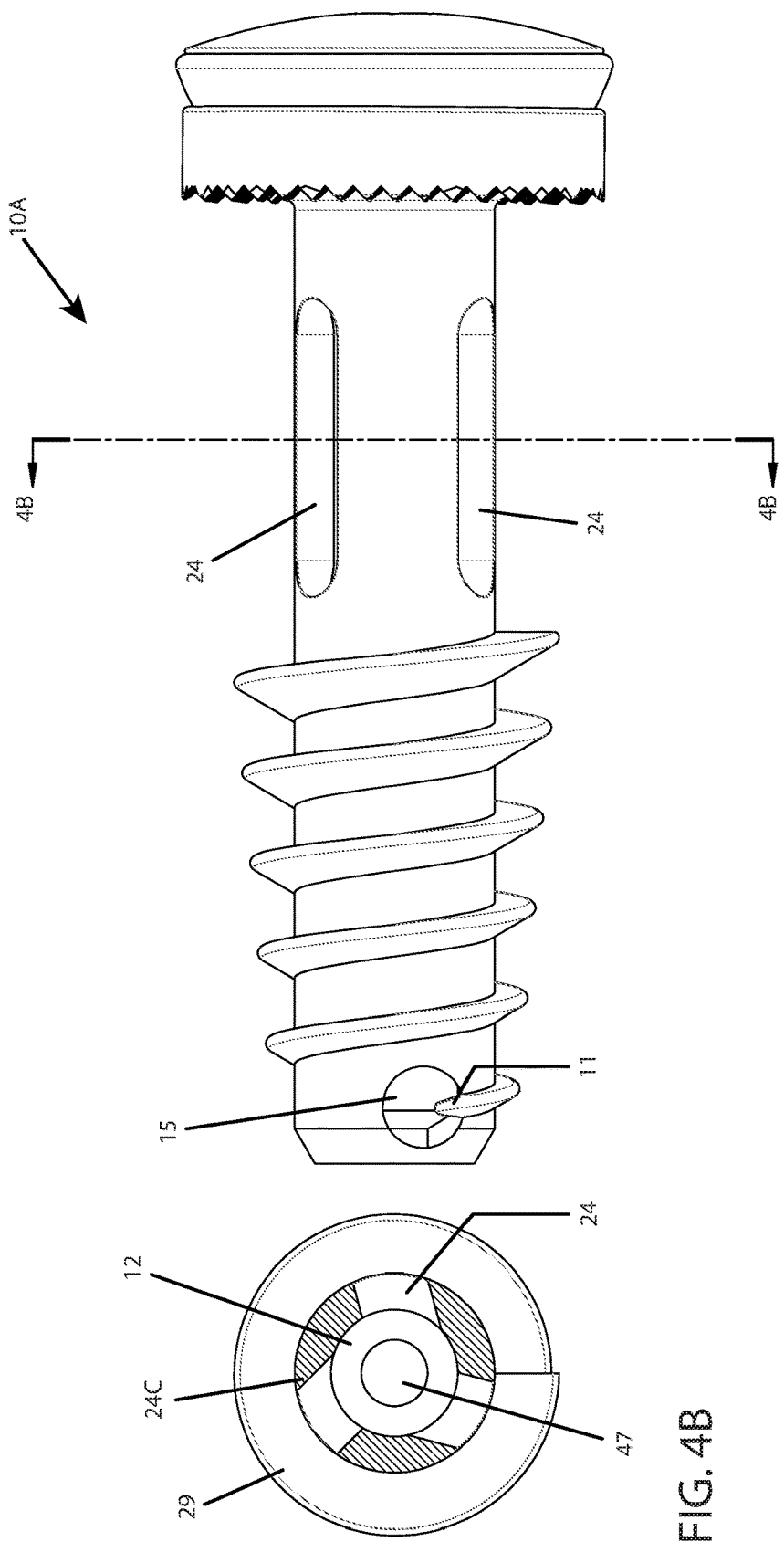
FIG. 4A is a plan view of a first embodiment of the present invention showing the counterclockwise cutting edges of the slotted windows.
FIG. 4B is a cross-sectional view taken along lines 4B-4B of FIG. 4A.

With reference to FIGS. 1-17; two versions or embodiments of an improved joint fixation screw 10A and 10B for a transiliac fixation are shown. Each embodiment has common features with variations on number of the cutting flutes and threads at or near the tip end. FIG. 4 shows the proximal head end opposite to the bone cutting tip end. The head 30 at this end is a common feature to each embodiment.

Each screw 10A and 10B has a hollow elongated shaft 20. The shaft 20 has an externally threaded end portion 21 and a smooth shank portion 25. The smooth shank portion 25 has a plurality of window openings 24 open to a chamber 12 inside the hollow shaft 20. At a proximal end of the screws 10A, 10B is an enlarged head 30. The center of the head 30 is a threaded opening 33 open to the chamber 12. The threaded end portion 21 of the hollow shaft 20 has threads 28, 29, these threads 28, 29 can be tapered with an increasing diameter towards the smooth portion of the shank, as shown in the figures. All these features are common to each screw 10A and 10B.

Figure 1:
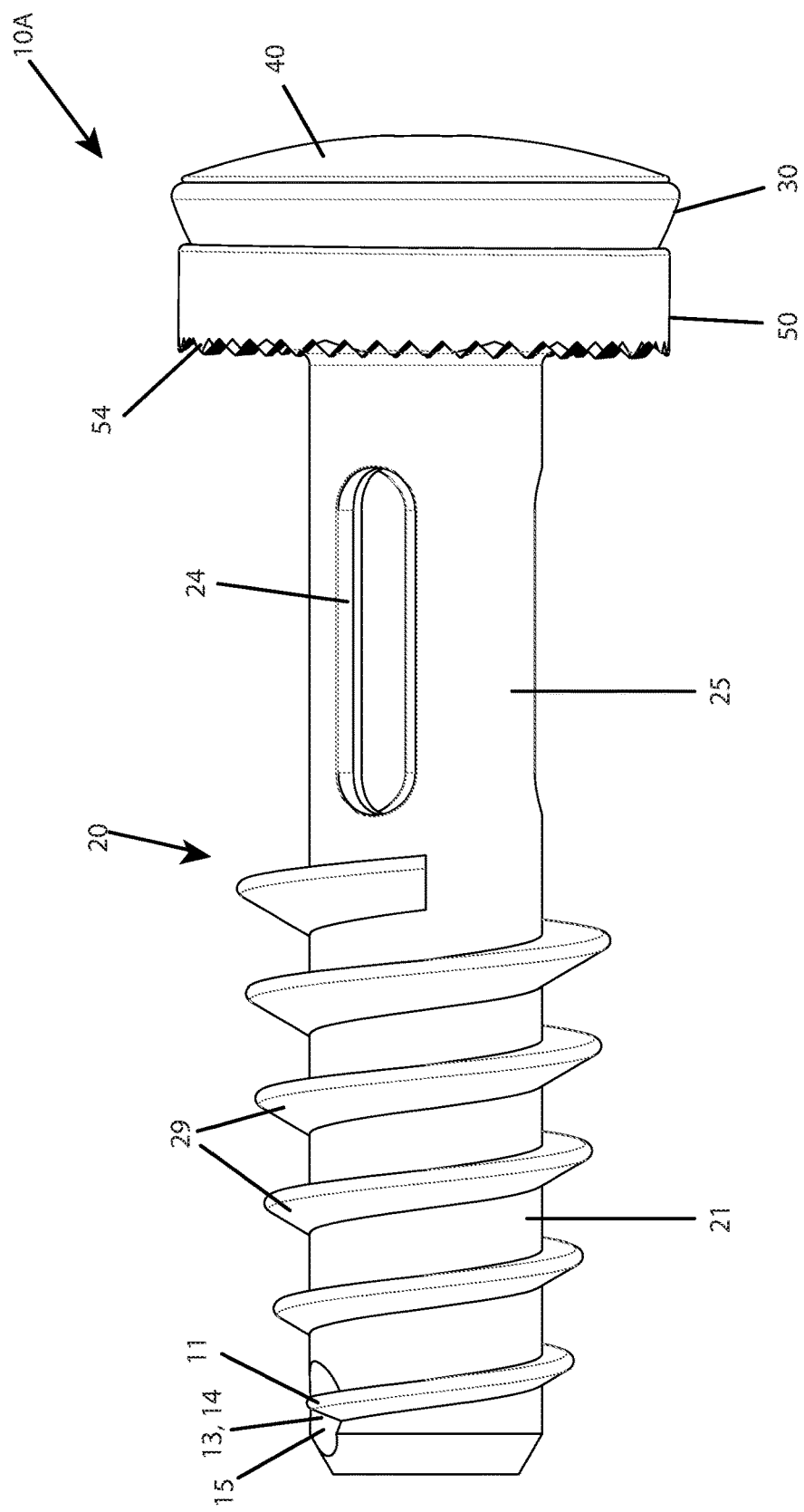
FIG. 1 is a plan view of a first embodiment of the present invention.
Figure 5:
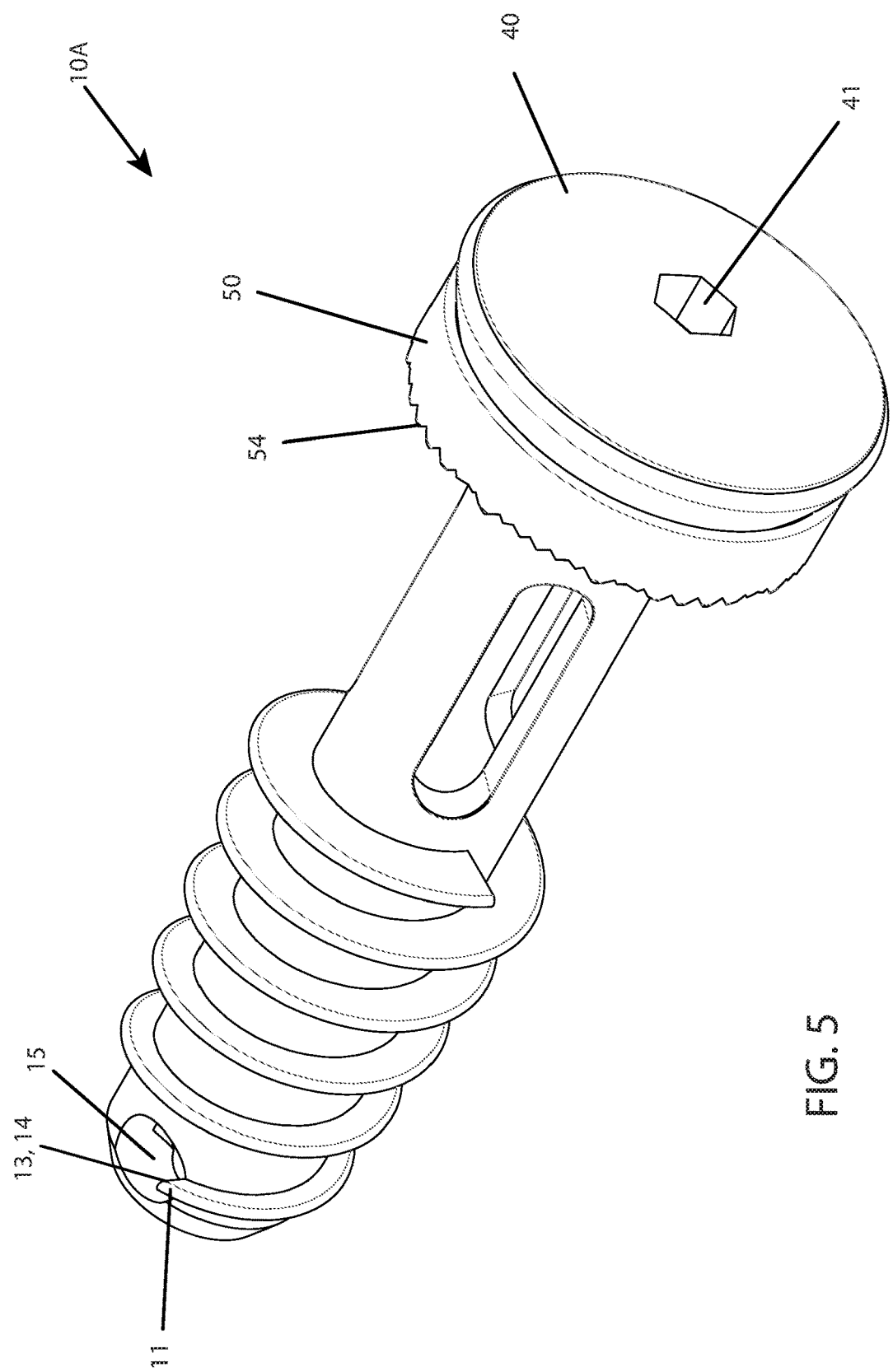
FIG. 5 is an isometric view of the first embodiment of the present invention.

In a first embodiment of FIGS. 1-8B, the screw 10A has one cutting flute 11. As shown in FIGS. 1, 4A and 5, the cutting edge 13 lies in a plane almost or substantially parallel to the axis of the screw shaft and each had a ramp 14 for directing bone fragments to a bone receiving opening 15 into the hollow chamber 12 and is preferably oriented perpendicular to the helical thread start. The cut fragments spiral along the ramped surfaces 14 where they bend and break into bone fragments as they enter the opening 15.

With reference to FIGS. 8A and 8B, an exploded view of the first embodiment shows a washer 50 with a concavity 52 in the form of a polyaxial shaped bowl to receive the bottom 32 of the head 30 which has a rounded or polyaxial hemispherical curvature. This feature allows the washer 50 to occupy a space between the screw head 30 and the bone on tightening and can accommodate any angulation so the washer 50 stays flush against the bone. In the absence of this feature, the screw head bottom 32 could be tilted and the washer 50 would not be flush to the bone surface.

In a second embodiment of FIGS. 9-16B, there are two cutting flutes 11, one flute 11 at each start of the threads 28, 29 directly in front of and partially overhanging a bone receiving opening 15. Each flute 11 is diametrically opposed from the other and each has a cutting edge 13 formed from a start or leading end of a thread 28, 29 at or near the tip end 21. The cutting edges 13 are still circumferentially in a plane about parallel to the axis, but are positioned diametrically opposite at each thread start and overhanging the opening 15 ahead of the flutes 11. Both flutes 11 capture the cut bone fragments and direct them into the chamber 12 in pieces that are broken on threading by having the ramp surfaces 14 pushing the bone fragments into the openings 15 during implantation.

Figure 2:
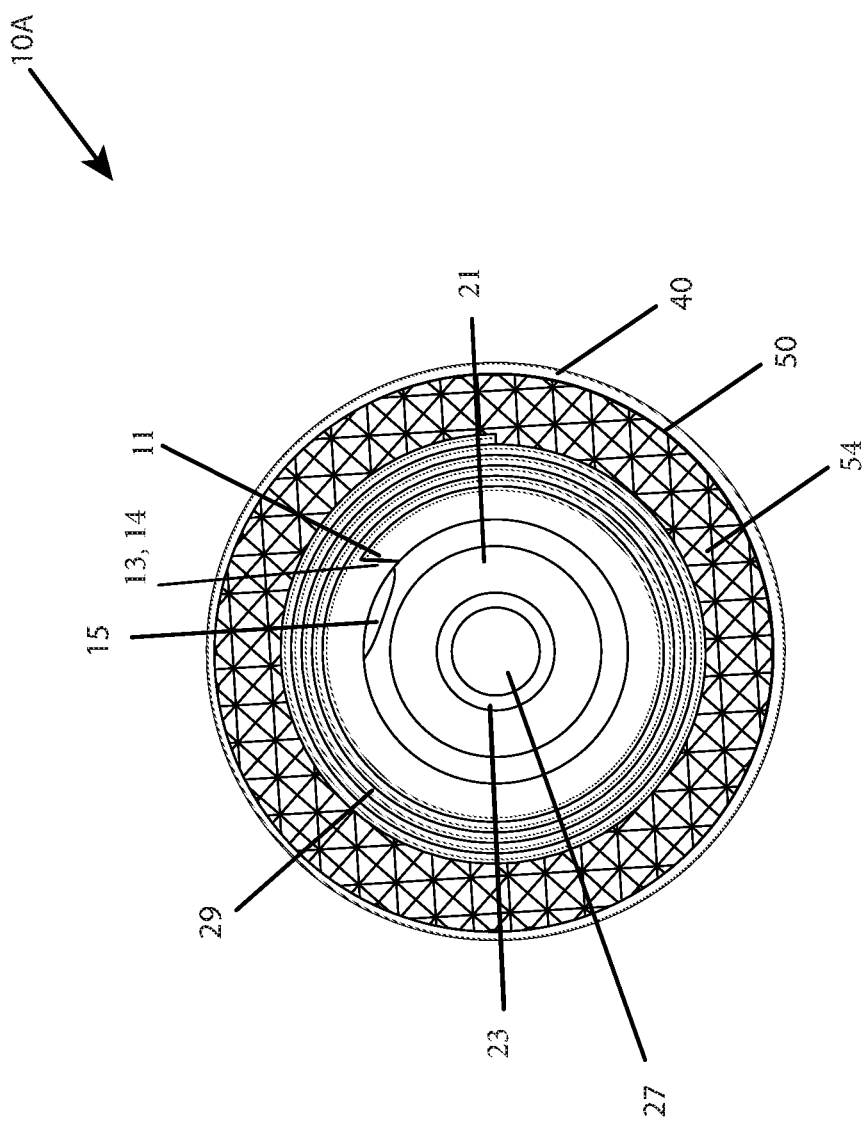
FIG. 2 is an end view looking towards the distal end of the screw of the present invention.
Figure 3:
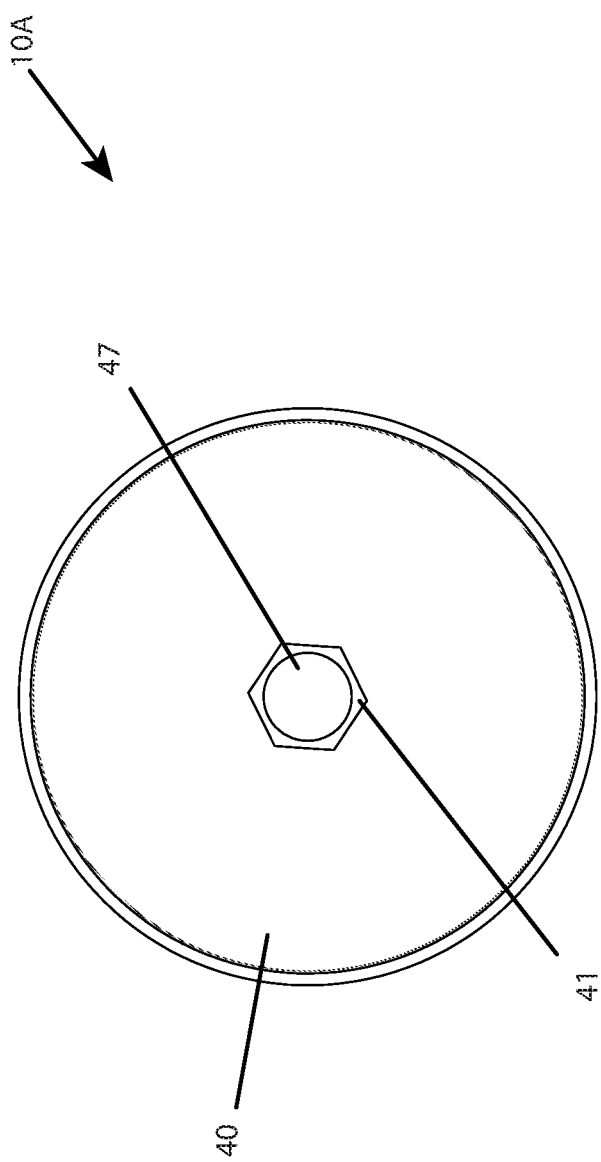
FIG. 3 is a top view of the screw of the first embodiment of the present invention.

With reference to FIGS. 2, 7A, 10 and 15B, a third embodiment, an annular ledge 23 extends across the hollow shaft 20 at the tip end 21. The ledge 23 has an aperture 27 for receiving a guide wire. This third version screw has the same flutes 11 as shown in FIG. 1 or 2.

FIGS. 7A-8B and FIGS. 15A-16B show a threaded driver cap 40 with tool aperture 41 inserted and threaded into the threads 33 of the enlarged head 30. This screw head 30 has a torque receiving cavity 41A with projections 42 to receive a torqueing tool to implant the screw 10A, 10B. Centrally, there is an aperture 47 to allow the screw to pass over a guide wire along a directional pre-drilled path.

As the screw 10A, 10B is torqued into the pre-drilled pilot hole, the cutting flutes 11 create autograft bone fragments that are delivered directly into the chamber 12. In this way, the patient's bone fragments are made available to enhance new bone growth to fuse the screw 10A, 10B in place.

One purpose of this invention is to direct bone that is cut by the self-tapping threads and cutting edge or edges 13 at or near the tip of the bone screw 10A, 10B or otherwise gathered by the flutes 11 and directed into the internal chamber 12 of the screw to serve as additional autograft material. Previously, this material would be compressed into the bone around the outside of the screw. The screw would be filled with previously harvested autograft material which could be packed into the screw from an opening in the head end of the screw. The screw is used to secure two bones together, in this case the sacrum and the ilium. When preparing the bone to accept the screw, a hole will be drilled and tapped to a size smaller than the actual screw. The screw can be packed with graft material prior to implantation. The self-tapping edge of the screw will cut additional autograft material as it is installed and the flute will direct this freshly cut autograft material to join the existing material in the inner chamber 12 of the screw. Some of this material will be pushed out of the plurality of window openings 24 or fenestrations in the shaft 20 of the screw as it is tightened to aid in fusion around and into the body of the screw. Many variations of similar flute shapes will produce a similar result. The screw material can be anything hard and strong enough to cut and direct bone chips and withstand the biomechanical loads of the application, preferably titanium, stainless steel or alloys of these materials or metals will work satisfactorily.

Figure 6:
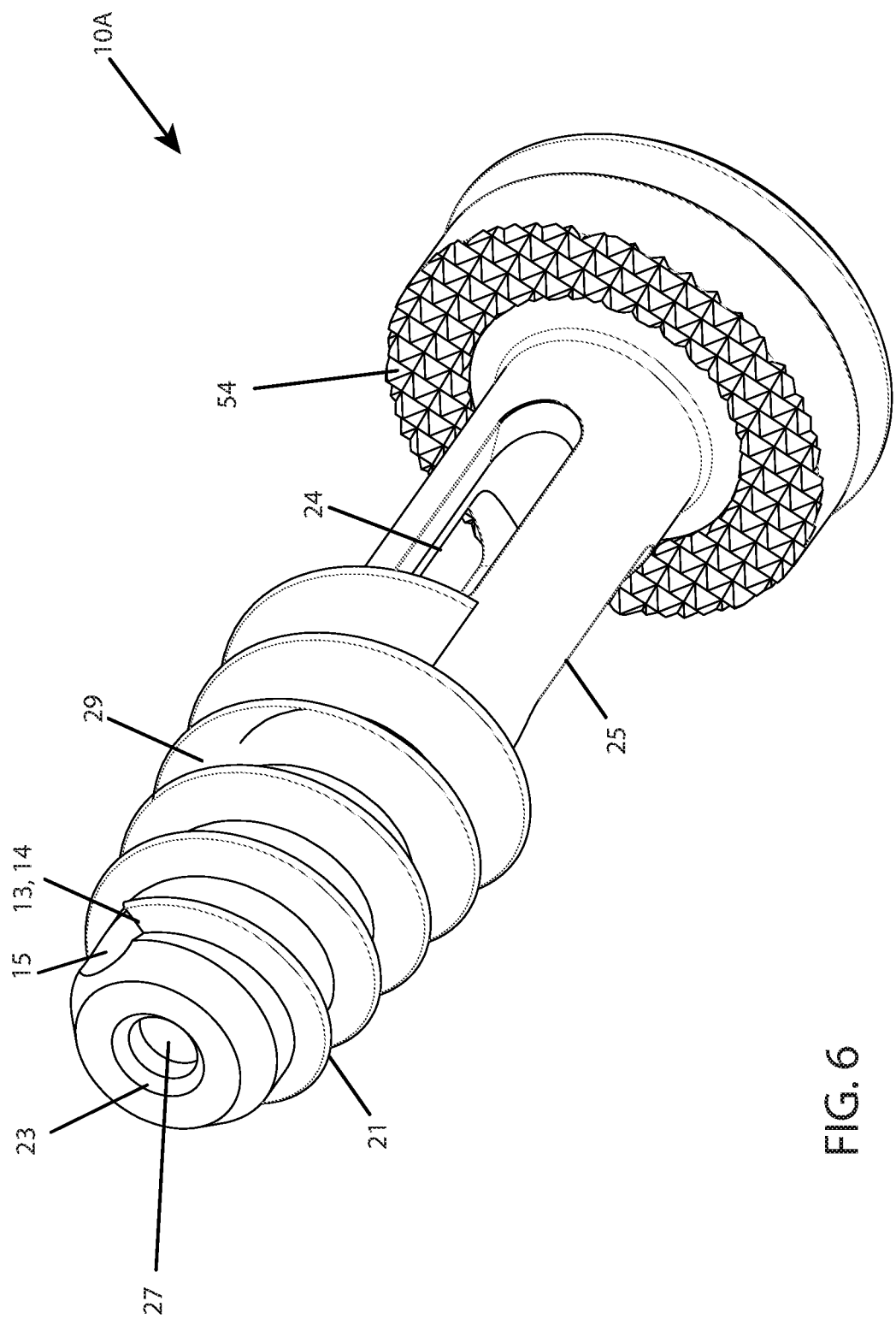
FIG. 6 is a second isometric or perspective view showing the bottom of the screw of the present invention.
Figure 9:
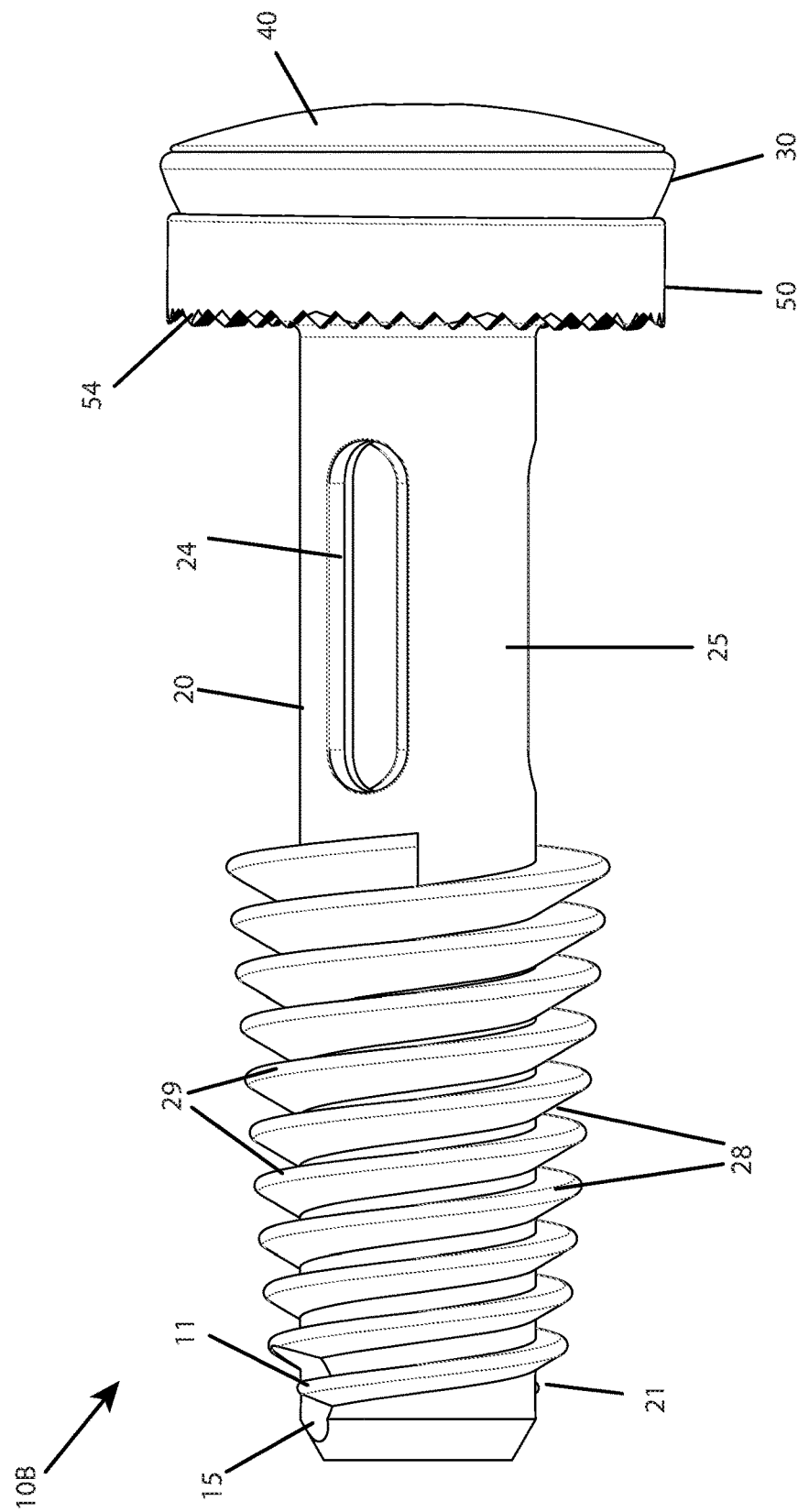
FIG. 9 is a side view or plan view of a second embodiment of the present invention exhibiting a dual threaded shank.

The present invention SI (Sacro-iliac) screw described herein has shown several important features of this screw. These features include: the lagging where the head 30 is pulled down by the coarse threads 29 or 28, 29 and the lagged portion is within the smooth shank portion 25 and not engaged by threads 29; the screw has a large bore or chamber 12 for inserting bone graft with the option to cap this bore which communicates to the SI space after insertion with the driver cap 40; the shaft 20 has only the single or dual threaded end portion 21 to engage only the sacrum bone, the ilium bone is positioned on the smooth shank portion 25; an optional anti-back out feature of the washer 50 under the head 30 in the form of a series of wedge-shaped teeth 54 to engage the iliac bone surface can be used as shown in FIG. 6. Optionally, a wedge-shaped washer 50 could be used under the screw head 30 to accommodate the surface angle of the ilium with respect to the screw axis and also employ an anti-back out feature shown in FIG. 6, but as a separate feature on the washer 50.

Figures 12A, 12B:
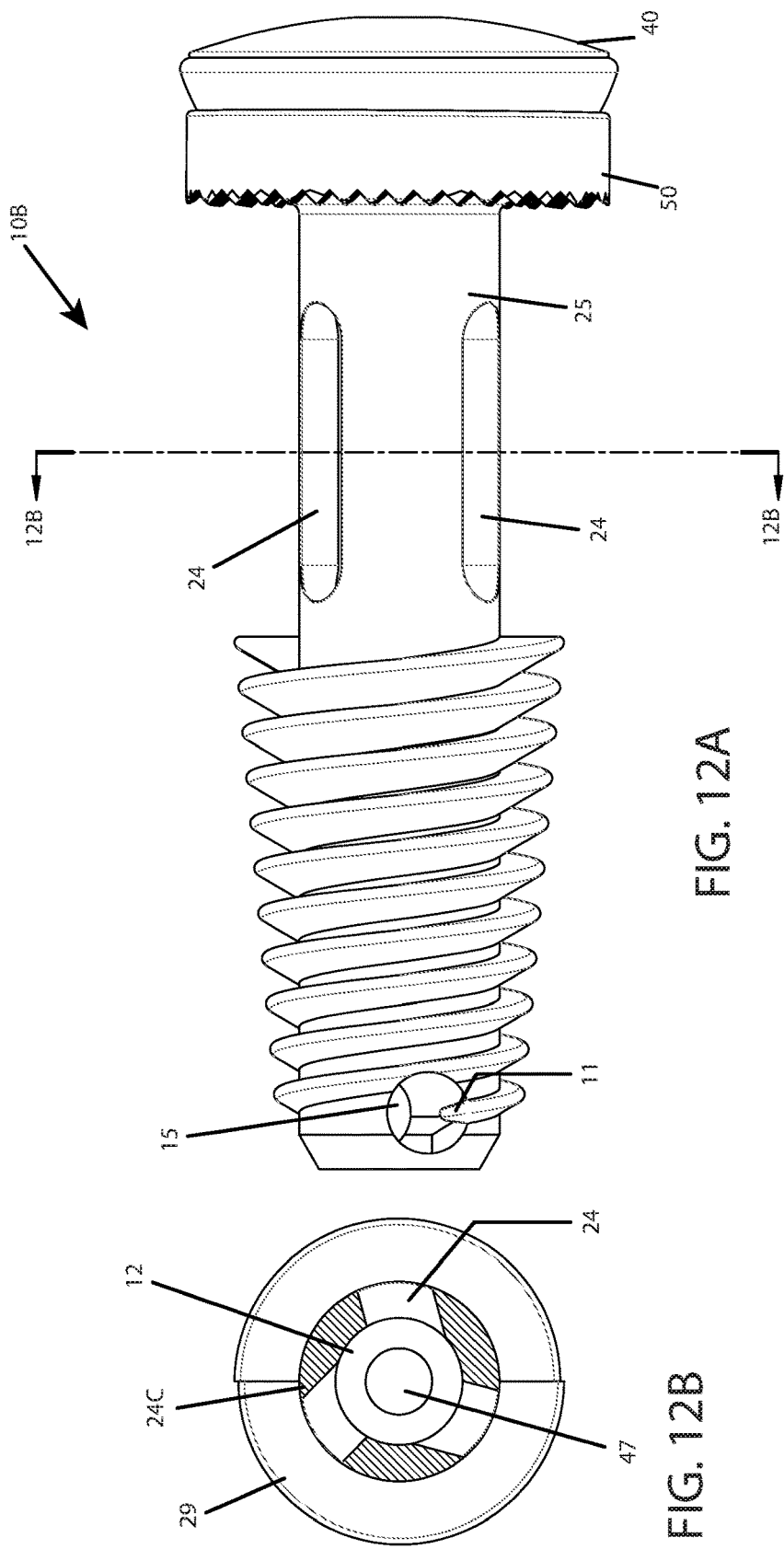
FIG. 12A is a side view of the second embodiment of the present invention.
FIG. 12B is a cross-sectional view taken along lines 12B-12B showing the counterclockwise cutting edges on the slotted windows.
Figure 13:
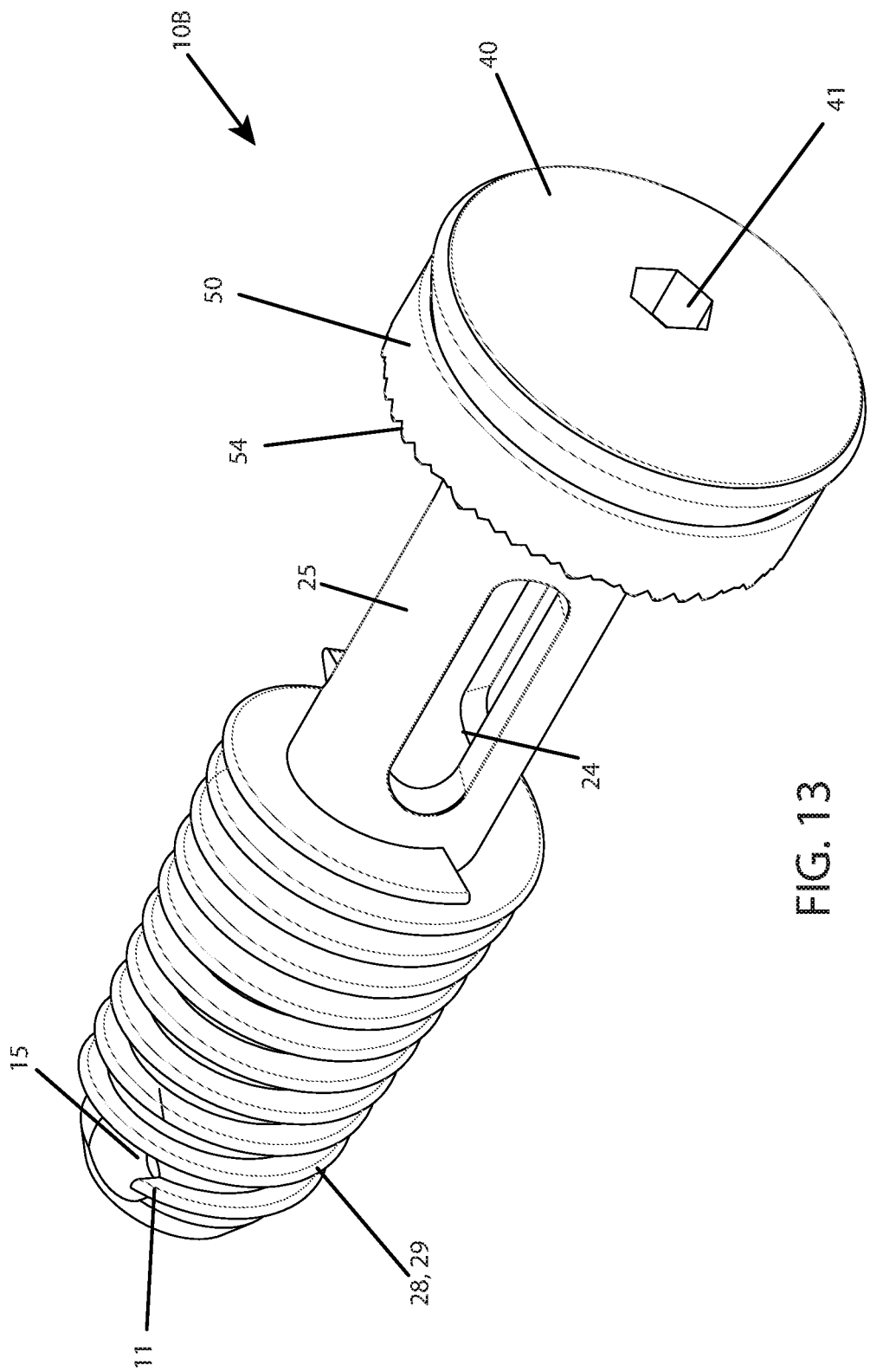
FIG. 13 is an isometric view taken from the top end of the second embodiment of the present invention.
Figure 14:
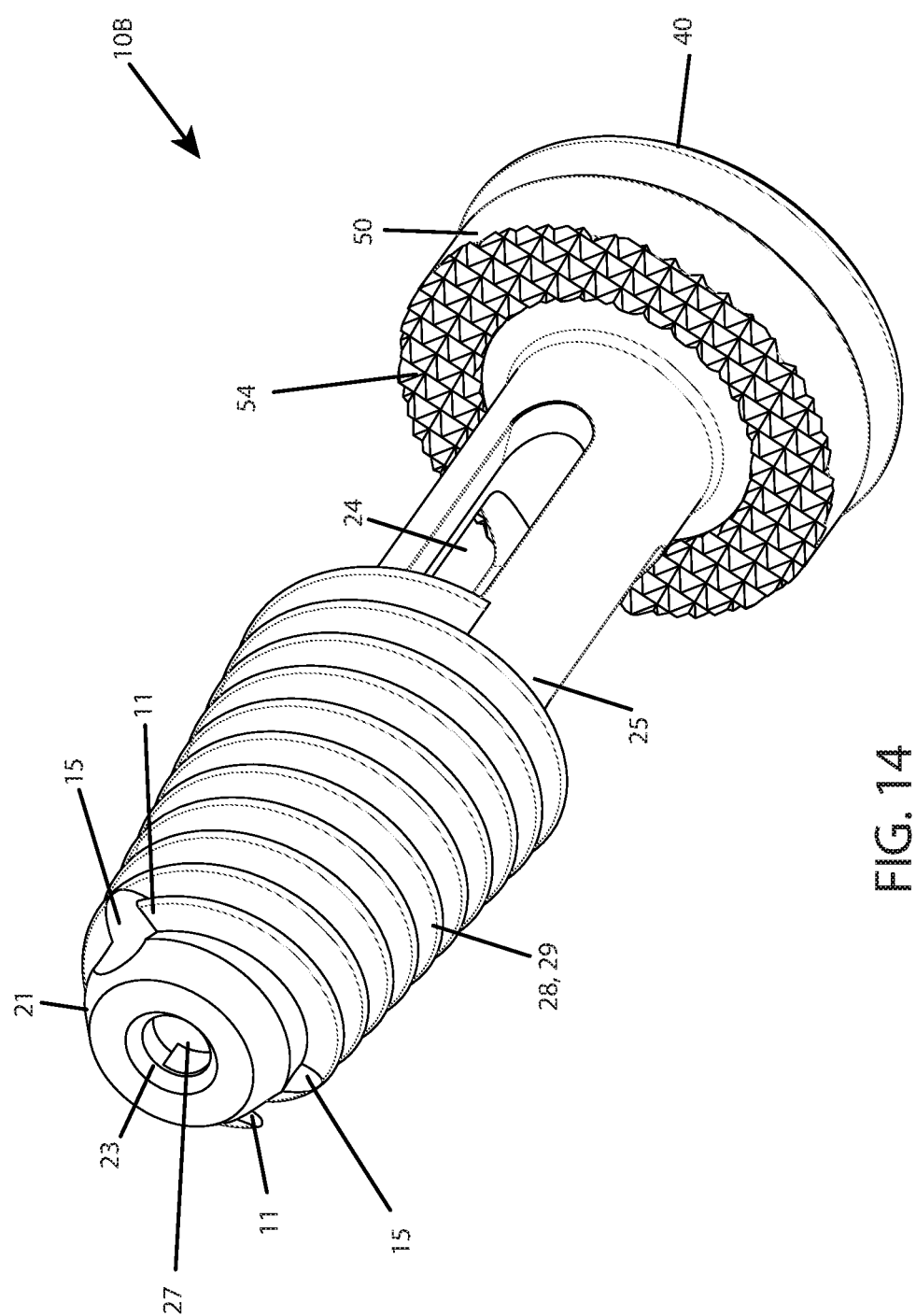
FIG. 14 is a bottom view of the second embodiment of the present invention.

With reference to FIGS. 4B and 12B, the window openings 24, the longitudinal edges 24C of at least one side or both sides of each window 24 can optionally be configured with sharp edges 24C for cutting bone. The use of this feature is not needed during insertion of the screw, however, if the patient experiences any complications later or particularly after a few months, a surgeon may want to remove the screw 10A, 10B. With the cutting edges 24C on the side of the window 24, or facing the edges 24C on a counterclockwise untightening position, facing the bone when the screw is untightened, when the counterclockwise rotation is made, the newly formed bone can easily be cut away to facilitate screw removal by the side having the bone cutting edge 24C. Absent this feature, newly formed bone will make removal very difficult.

With reference to FIGS. 7A-8B and 15A-16B, particular attention is drawn to the end cap 40 which has a threaded male end 43 for engaging a female threaded portion 33 to fix the cap 40 to the screw body or shaft 20. This removable threaded cap 40 allows the addition of autograft or allograft bone or other biocompatible and bioactive materials to be added to the screw 10A or 10B after implantation during the surgical procedure. The removed cap 40 exposes torque driving aperture 41A in the screw head 30 for receiving a bit or end of an implantation tool. Once implanted, the screw 10A or 10B can be filled with material and the end cap 40 installed.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A method of transiliac fixation comprises the steps of:
   pre-drilling an opening in the sacrum and the ilium bones to be fixed with a pilot hole opening; and
   inserting by rotating a threaded joint fixation screw with a hollow shaft and with one or more bone cutting threads and one or more cutting flutes, each cutting flute being at a start of a thread to direct bone fragments to a bone receiving opening and into the hollow shaft into the pre-drilled opening while cutting autograft bone fragments directed into the hollow shaft by threading the screw, wherein the hollow shaft has a bone receiving chamber extending to a plurality of openings further in the hollow shaft spaced above the threads along a smooth non-threaded shank portion of the screw and below a screw head and the step of threading of the screw directs the autograft bone fragments to the openings to enhance fusion.

2. The method of transiliac fixation of claim 1 wherein the screw has the aperture at a tip end and a driver cap at the screw head and the method further comprises the steps of:
   inserting a guide wire to create a drill path;
   inserting a cannulated drill over the guide wire to pre-drill the hole; and
   inserting the screw onto the guide wire to direct the path for insertion into the bone.

3. The method of transiliac fixation of claim 1 wherein the step of inserting and threading the screw has the threads engage only the sacrum bone and the ilium bone is positioned onto the smooth non-threaded shank portion.

\* \* \* \* \*